US00PP10880P

United States Patent [19]

Roberson

[11] Patent Number: Plant 10,880

[45] Date of Patent: May 4, 1999

[54] LANTANA PLANT NAMED 'ROBPATDOV'

[76] Inventor: Robert J. Roberson, 31706 E. Pink Hill Rd., Grain Valley, Jackson County, Mo. 64029

[21] Appl. No.: 08/841,308

[22] Filed: Apr. 30, 1997

[51] Int. Cl.[6] ..... A01H 5/00

[52] U.S. Cl. ..... Plt./227

[58] Field of Search ..... Plt./54.1, 227

*Primary Examiner*—Howard J. Locker
*Assistant Examiner*—Kent L. Bell
*Attorney, Agent, or Firm*—Rothwell, Figg, Ernst & Kurz

[57] ABSTRACT

This invention relates to a new and distinct *Lantana camara* cultivar which is outstanding because of its 1) "truer" white floret color; 2) thin, gracilis stems with very prostrate or trailing growth habit; 3) very intense fragrance; 4) self-branching and dense, "compact-like" (short internodes) growth; 5) moderate or controlled growth habit; and 6) very nearly sterile reproductive state.

1 Drawing Sheet

SUMMARY OF THE INVENTION

This invention relates to a new and distinct *Lantana camara* cultivar which is outstanding because of its 1) "truer" white floret color; 2) thin, gracilis stems with very prostrate or trailing growth habit; 3) very intense fragrance; 4) self-branching and dense, "compact-like" (short internodes) growth; 5) moderate or controlled growth habit; 6) very nearly sterile reproductive state and was primarily selected for these characteristics. This selection was made from a specially designed Lantana hybridizing program with said hybrid cultivars being planted and grown in Grain Valley, Mo.

ORIGIN AND ASEXUAL REPRODUCTION

Asexual reproduction of this cultivar by tip cuttings was directed by me, such reproduction establishing that the plant does in fact maintain the characteristics described, in successive generations.

It should be noted that the plant was initially selected from a Lantana planting being grown near Grain Valley, Mo. in a cultivated area and has since been reproduced by tip cuttings in the vicinity of Grain Valley, Mo. with the new and distinct characteristics stated herein, found to be maintained through successive generations as before recited.

*Lantana camara* is native to the subtropics and tropical North and South America. They are woody ornamentals which are not usually winter hardy North of USDA horticulture Zone 9. The roughish leaves range from yellow-green to green to blue-green and the two basic growth forms are mounding and trailing (weeping). Bloom color usually include yellow, white, cream, pink, or orange.

The cultivar of *Lantana camara* 'Robpatdov' may further be described as having a number of distinctive characteristics which are enumerated in the succeeding specific description but broadly stated as comprising a 1) "truer" white floret color; 2) thin, gracilis stems with very prostrate or trailing growth habit; 3) very intense fragrance; 4) self-branching and dense, "compact-like" (short internodes) growth; 5) moderate or controlled growth habit; 6) very nearly sterile reproductive state and was primarily selected for these characteristics.

I have chosen to identify this new cultivar as *Lantana camara* 'Robpatdov'. This cultivar is being marketed in the United States under the name of Patriot(™) Dove Wings.

BRIEF DESCRIPTION OF THE DRAWING

The accompanying

DETAILED DESCRIPTION

Figure 1:
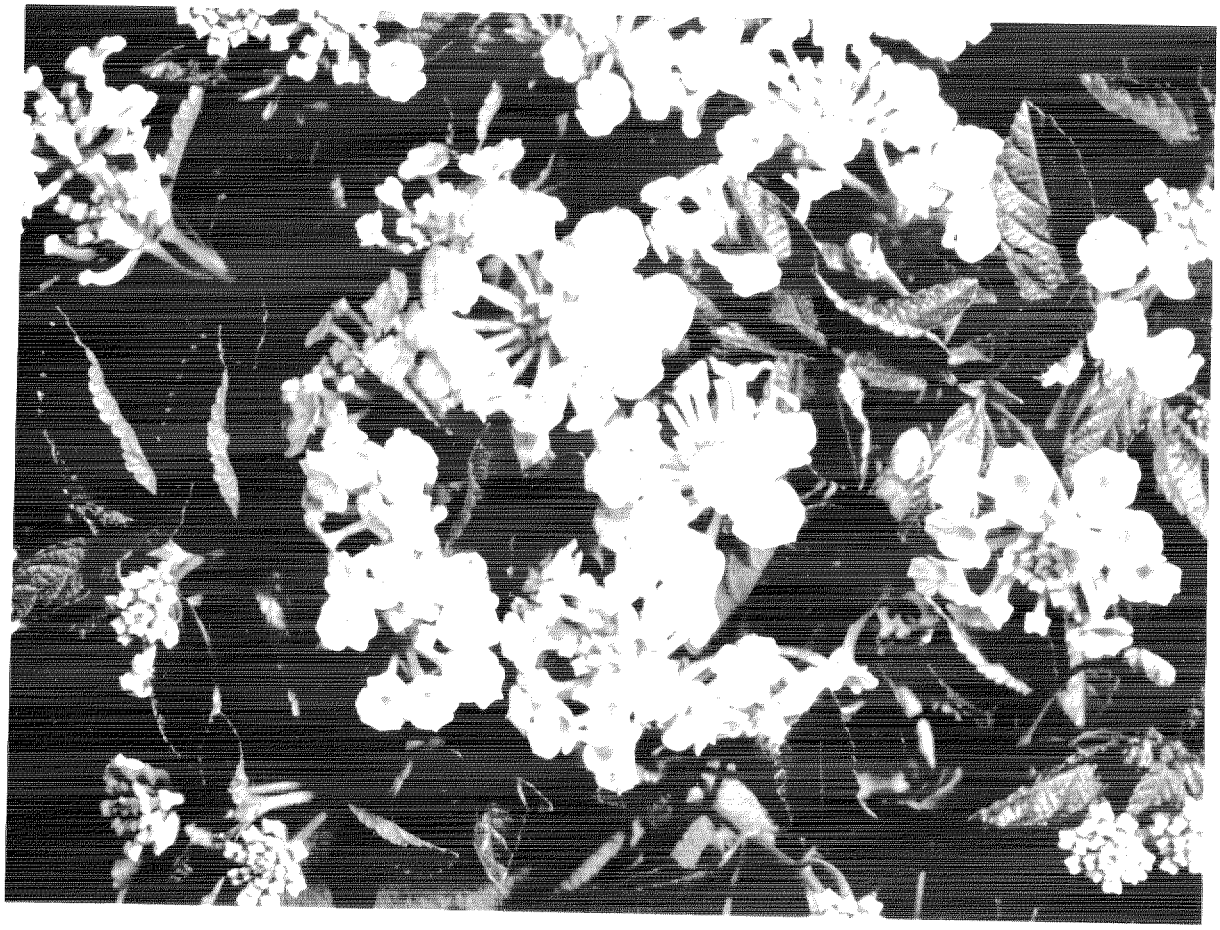
FIG. 1 shows as nearly true as it is reasonably possible to make the same, in color illustration of this character, typical leaves and flowers of the new variety. The photographic drawing illustrates the flower form and color and the foliage habit and color.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo.

Parentage:

*Seed parent.*—*Lantana camara* Patriot(™) Snowfall (unpatented) (in a semicontrolled open pollination).

*Pollen parent.*—Unknown.

Propagation: Asexual reproduction by tip cuttings started near Grain Valley, Mo.

Plant descriptions:

*Inflorescence and reproductive parts.*—The inflorescence is a flat topped round cluster of 25–30 florets. The individual clusters are determinate and arise from the leaf axils. Each individual floret is slightly un-symmetrical with a bilateral symmetry and is subtended by a single bract. The perianth consists of: the Calyx (5 united-sepals) and the Corolla (5 united petals with narrow tube). The flowers are zygomorphic, hermaphroditic, and have 4 introse stamens which are didynamous. The ovary is superior, the style is terminal, and the stigma is lobed. The ovary is 2 locular, but is divided into 4 loculi by a false septum in each loculus. The placentation is axile with 2 ovules per carpel. The fruit classification is drupe and potentially contains 2 seeds. When fruit forms, it is medium olive green (PMS#379); then matures through a darker green (PMS#385) to a near black (PMS#439).

*Inflorescence dimensions.*—Bloom cluster — 1.0" in diameter. Single Floret — 0.18". Pedicle length — 1.1". Corolla tube — 0.35".

*Inflorescence colors.*—Buds — Pale cream-yellow (PMS#127). First opening — white with yellow eye (PMS#129). Maturity — Pure white. Tube — white.

*Developmental pattern.*—First flowers develop in a circular pattern on the periphery of the inflorescence.

*Branching.*—Due to self-branching and shorter (1½ inch) than average (2½ to 3 inches) internode spacing, this plant maintains an above-average density without any pinching.

*Height and spread.*—In one growing season, i.e., frost to frost May 5 to September 28, in USDA zone 5) 'Robpatdov' reaches a height of 1 foot by 2 feet wide.

*Vigor.*—Newly rooted (two week old) tip cuttings maintained in a greenhouse at 70° F. night temperature and 85° F. day temperature with 16 hour full sun days will result in approximately ¾ inch growth per week.

*Leaves and stems.*—Leaf shape: Ovate. Leaf margins: Serrate. Leaf tip and base: Acute. Leaf veins: Pinnate. Leaf surface: Rough due to bristly hairs. Leaf arrangement: Opposite. Leaf color: Immature leaves are medium light green (PMS #370) and mature leaves are medium green (PMS #364). Leaf size: Length 1.02". Petiole 0.20". Width 0.7". Stem: The stems on a 60-day old tip cutting are an average of 3/32 inch (about 50% of the stem thickness of the average *Lantana camara's* grown). Square in youth becoming round and woody with age.

*Roots*: Highly branched and fibrous.

*Flowering time:* The color display begins blooming at 6–7 weeks after cuttings are made, or 4 weeks after potting, and continue until temperatures drop below 45 degrees Fahrenheit.

Diseases: No unusual susceptibility to diseases noted to date.

Insects: Typical of this plant genus, white flies can be attracted to Lantana. There are no other insect problems known at this time.

GENERAL OBSERVATIONS

*Lantana camara* 'Robpatdov', with its 1) "truer" white floret color; 2) thin, gracilis stems with very prostrate or trailing growth habit; 3) very intense fragrance; 4) self-branching and dense, "compact-like" (short internodes) growth; 5) moderate or controlled growth habit; 6) very nearly sterile reproductive state is an improved *Lantana camara* cultivar in both color and type (prostrate form).

For the purpose of ornamental horticulture in our present living environments which include very specialized and sophisticated gardeners and smaller yards and patio gardening, *Lantana camara* plant 'Robpatdov' is ideal due to several characteristics:

A. The endless search for truly "white" flowers of any and all genera and the current demand for fragrance in the garden find their fulfillment in this new *Lantana camara*, 'Robpatdov'.

B. 'Robpatdov's' self-branching tendency, short internode spacing, thin graceful stem growth and very prostrate trailing habit make this cultivar ideal for today's popular patio gardening, smaller garden vinettes, container growing, and demand for ground covers.

C. 'Robpatadov' is a more manageable *Lantana camara* than most in the landscape due to its moderate or controlled growth habit and its near sterile reproductive state.

COMPARISON TO KNOWN VARIETIES

*Lantana camara* plant 'Robpatdov' should be compared with *Lantana camera* 'Silver Mound' (unpatented) as this is the best color comparison known in today's trade. The inflorescence form and color presentations of these two cultivars are somewhat similar. However, 'Robpatdov' is a "truer" white and is more compact, gracilis, and fragrant than 'Silver Mound', and thus better meets the present trends of todays gardening.

*Lantana camara* plant 'Robpatdov' should also be compared with the parent variety Patriot(™) Snowfall. The claimed variety blooms about 10–15% more profusely creating a more dense color mass than Patriot(™) Snowfall. Robpatdov sets 50% fewer seeds than Patriot (™) Snowfall, i.e., an average one season plant growth of Patriot(™) Snowfall would set 50 seeds and 'Robpatdov' approximately 25. 'Robpatdov' is more compact or dense due to the ⅓ shorter internode length and 20% stronger self-branching tendency. 'Robpatdov' give a more overall compat, dense appearance. 'Robpatdov' also has a more graceful (prostate or recumbent) habit due to stems being approximately 35% less in thickness than the stems of Patriot(™) Snowfall.

I claim:

1. A new and distinct cultivar of *Lantana camara* plant substantially as described and illustrated herein.

* * * * *